US006767496B1

(12) United States Patent
Jensen et al.

(10) Patent No.: US 6,767,496 B1
(45) Date of Patent: Jul. 27, 2004

(54) METHOD AND SYSTEM FOR THE PRODUCTION OF A PLASTIC NEEDLE

(75) Inventors: Søren Jensen, Taastrup (DK); Mogens Papsøe, Hørsholm (DK); Poul E. B. Nielsen, Vedbæk (DK); Henrik Egesborg Hansen, Hellerup (DK); Anne Sørensen, Holte (DK)

(73) Assignee: Novo Nordisk A/S (DK)

( * ) Notice: Subject to any disclaimer, the term of this patent is extended or adjusted under 35 U.S.C. 154(b) by 0 days.

(21) Appl. No.: 09/979,779

(22) PCT Filed: May 26, 2000

(86) PCT No.: PCT/DK00/00286
§ 371 (c)(1),
(2), (4) Date: Nov. 27, 2001

(87) PCT Pub. No.: WO00/72901
PCT Pub. Date: Dec. 7, 2000

(30) Foreign Application Priority Data

May 28, 1999 (DK) ........................................ 1999 00760

(51) Int. Cl.$^7$ ............................................... B29C 45/73
(52) U.S. Cl. ............. 264/328.16; 264/319; 264/328.13; 264/328.1
(58) Field of Search ............................ 264/328.13, 319, 264/327, 328.16, 154, 328.1, 328.9; 425/577, 542

(56) References Cited

U.S. PATENT DOCUMENTS

| | | | | | |
|---|---|---|---|---|---|
| 4,149,695 A | * | 4/1979 | Quick et al. | ................. | 249/82 |
| 4,750,877 A | * | 6/1988 | McFarlane | ................... | 425/573 |
| 5,078,700 A | * | 1/1992 | Lambert et al. | ............. | 604/264 |
| 5,217,671 A | * | 6/1993 | Moriuchi et al. | ........... | 264/313 |
| 5,620,639 A | * | 4/1997 | Stevens et al. | ............... | 264/85 |
| 5,660,864 A | * | 8/1997 | Schmidhalter | .............. | 425/145 |
| 5,989,473 A | * | 11/1999 | Haverty | ...................... | 264/279 |
| 6,235,230 B1 | * | 5/2001 | Puniello | ..................... | 264/278 |
| 6,325,950 B1 | * | 12/2001 | Hosokawa et al. | ........ | 264/1.33 |
| 6,355,196 B1 | * | 3/2002 | Kotnis et al. | ............... | 264/219 |

OTHER PUBLICATIONS

Rosato, Donald V. and Dominick V. Rosato. Injection Molding Handbook. 2nd ed. New York: Chapman and Hall, 1995. p. 265.*
Rosato, Donald V. and Dominick V. Rosato, Injection Molding Handbook, 2nd ed. (1995). Chapman and Hall. pp. 173–174,259–260.*

* cited by examiner

Primary Examiner—Michael Colaianni
Assistant Examiner—Monica A. Fontaine
(74) Attorney, Agent, or Firm—Stites & Harbison PLLC; Marvin Petry

(57) ABSTRACT

A method and a system is provided for producing a needle of plastic, as well as the needle of plastic which includes a needle for medical purposes. The method for producing the needle includes introducing a melt of plastic into a feed system, increasing the melt pressure gradually during melt passage through the feed system, passing the melt into the mould cavity, whereby the melt substantially fills the mould cavity, cooling the melt into the mould cavity whereby the melt solidifies to a needle, and removing the needle from the mould cavity. Increasing the pressure through the feed system provides for meeting specific pressure demands at the entrance of the mould cavity, thereby moulding thin and elongated articles.

6 Claims, 5 Drawing Sheets

US 6,767,496 B1

METHOD AND SYSTEM FOR THE PRODUCTION OF A PLASTIC NEEDLE

TECHNICAL FIELD

Figure 1:
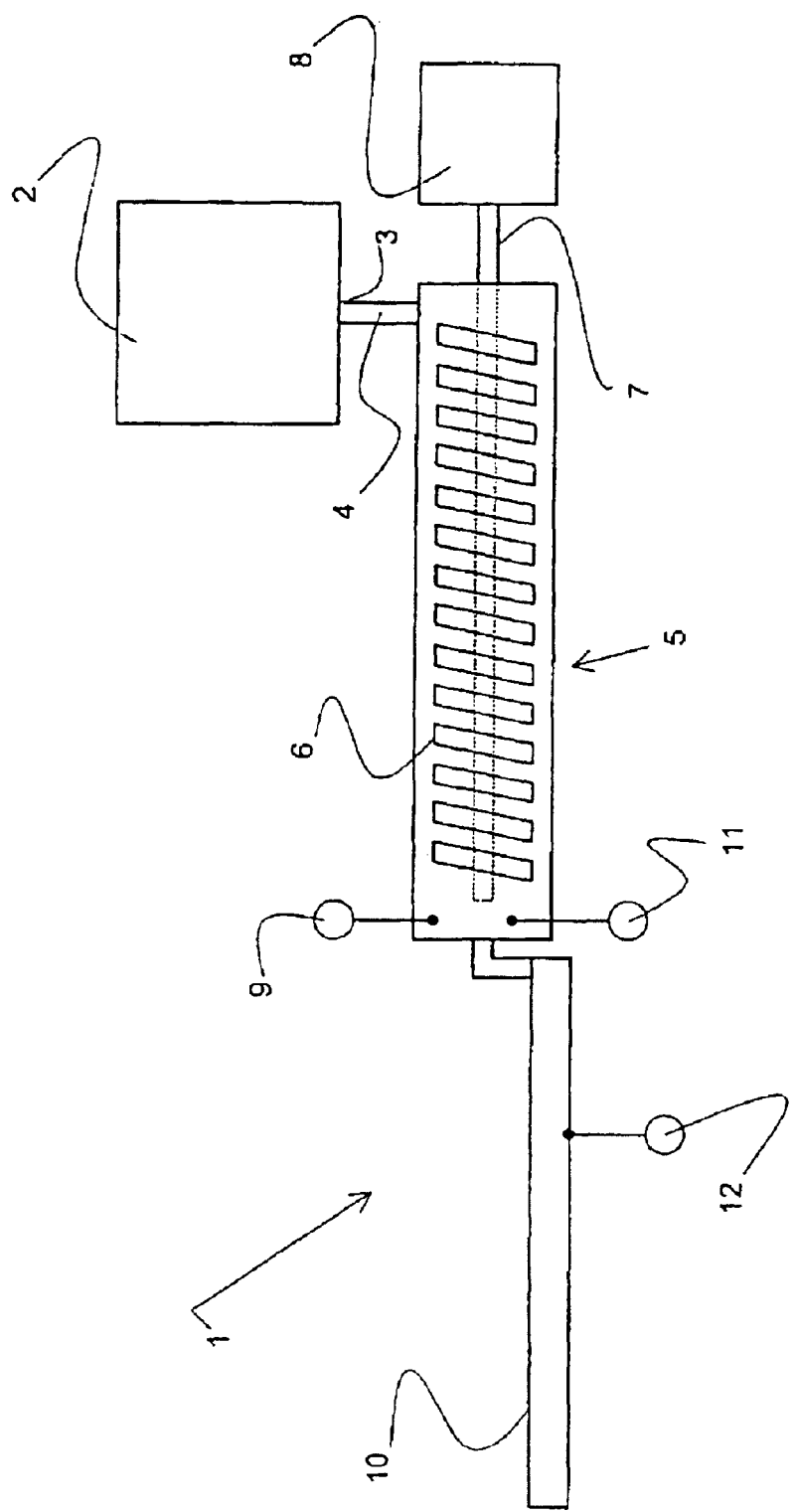

This invention relates to a method for producing a needle of plastic, a system for same as well as a needle of plastic, in particular a needle for medical purposes.

PRIOR ART

Needles or cannulas for medical purposes, such as injections of medicine, have been produced in various sizes depending on their intended use. For medicine to be injected frequently, such as several times a day, it is preferred to use the thinnest possible needle taking into account the viscosity of the medicine to be injected. Diabetics injecting insulin several times a day would preferably use a very thin needle, such as from gauge 26 to gauge 30, in order to reduce the pain as well as reduce the tissue damage resulting from each injection. In the present context the term "thin" refers to the diameter of the needle in question. Usually needles and other medical tubings are sized in gauges, wherein gauge 8 corresponds to 4.19 mm, and gauge 30 corresponds to 0.30 mm, for example.

In order to obtain a needle exhibiting the necessary strength for penetrating the skin and subcutis as part of the injection the very thin needles have usually been made from metal. Like many other medical articles it is of interest to produce the needles of a plastic material.

EP 452 595 discloses a method for producing a plastic medical tubing, such as a catheter, wherein a liquid crystalline polymer has been shear-thinned to such a viscosity allowing the melt to flow into and fill a mould. The plastic tubings produced have a gauge size of from 8 to 26, preferably from 14 to 20. The shear-thinning is provided by passing the plastic melt through an orifice before the melt reaches the mould. The patent describes a method for preparing the tubing by extruding the shear-thinned polymer into a mould, and describes further that the polymer melt may be forced under pressure through the orifice and thence directly into the mould.

However, in order to obtain very thin needles of the length relevant for injection of medicine very small volumes of plastic melt is used. It has been found, that merely extruding the melt, optionally under pressure will not result in the moulding of a needle of the dimensions in question with sufficient strength.

Injection moulding systems are often used for the production of large amount of articles. Injection moulding is a periodical process, in which a plastic granulate is being homogenized and melted by heating as well as by mechanical working. The plastic melt is injected into a mould cavity. The mould cavity has a temperature which is controlled to be lower than the melting point of the plastic. Hereby the melt injected into the mould cavity will solidify from the wall of the mould cavity to the centre of the article.

In the known injection moulding systems a screw may be used to the mechanical working of the melt as well as to introduce the melt into the mould cavity at a certain injection speed.

The screw movement or injection stroke is normally set to 1 to 4 times of the diameter of the screw. Hereby a right quality of the melt as well as a uniform shot volume will be ensured. By "shot volume" is meant the amount of melt necessary to at least fill the mould cavity to obtain a needle of predetermined dimensions.

The inertia of the screw as well as the hydraulic pressure transferred to the screw ensures in the known systems a pressure which is sufficient to fill large shot volumes.

However due to the small amount of melt necessary for producing a small article pressure applied to the screw cannot be timely transferred to the melt at the entrance of the mould cavity. The matter is that the hydraulic pressure behind the screw shall build up a pressure from the screw to the entrance of the mould cavity in approximately 1 to 10 msec, which has not been possible in known injection moulding system. Therefore, it has not previously been possible to obtain plastic needles or cannulas for medical purposes, for which the outer diameter of the needle or the cannula is 0.5 mm or less.

Furthermore, needles or cannulas of this diameter having an inner diameter is very thin-walled, a wall thickness of approximately 0.10–0.18 mm. This provides the problem of introducing the melt into the mould cavity in such a short time, that "freezing" of the melt is avoided. By "freezing" is meant that the melt solidifies rapidly due to the small thickness of the material. In case melt freezes in the first part of the mould cavity, the melt will not be able to fill the entire mould cavity and thereby a needle of predetermined dimensions will not be obtained.

By the known methods of injection moulding it has therefore not previously been possible to mould needles or cannulas having a wall thickness of material of approximately 0.10–0.18 mm.

The needles or cannulas are furthermore having a very large L/D ratio (wherein L is the length, and D is the diameter of the article) which further provides the problem of not only requiring a small shot volume but also of filling the "long" mould cavity as compared to a small diameter. Thus, in order to ensure that the mould cavity is filled totally with melt a very precise control of the energy reserve in the melt at the entrance of the mould cavity is necessary.

Certain requirements must be met for needles Or cannulas for medical purposes irrespective of the material used. One requirement is that the needle must not bend during insertion of the needle into the patient. Many plastic needles have lacked sufficiently strength when the diameter of the needle is decreased, so that in practice it has not been possible to use plastic needles for medical purposes unless very large needles, such as needles having a diameter of 1 mm or above.

CORE OF THE INVENTION

One aspect of the invention relates to a method for producing a plastic needle, which needle has two ends, wherein at least the outer diameter of one end is less than 0.50 mm, said needle further having a longitudinal lumen extending between two openings of the needle, in a moulding system having an assembly comprising a feed system and a mould cavity, said method comprising the following steps:
 introducing a melt of plastic into the feed system,
 increasing the melt pressure gradually during melt passage through the feed system,
 passing the melt into the mould cavity, whereby the melt substantially fills the mould cavity,
 cooling the melt in the mould cavity whereby the melt solidifies to a needle, and
 removing the needle from the mould cavity.

Another aspect of the invention is a system for producing a hollow plastic needle, having an assembly comprising a feed system and a mould cavity, and further comprising means for introducing a melt of plastic into the feed system, said feed system being arranged for increasing the melt pressure gradually during melt passage through the feed system, and means for passing the melt into the mould cavity, so that the melt substantially fills the mould cavity.

By the present invention it has been found that in order to produce small, thin and elongated articles by injection moulding whereby the shot volume is very small it is required to ensure a high energy reserve in the melt at the entrance of the mould cavity itself.

By gradually increasing the pressure through the feed system it is possible to meet the specific pressure demands at the entrance of the mould cavity in order to mould the thin and elongated articles in spite of the small shot volume, because the melt will then reach a sufficient pressure before it enters the mould cavity.

During injection moulding the melt is in motion in the feed system, i.e. flows, whereby the flow front of the melt has a pressure of approximately 0.1 MPa whereas the pressure in front of the screw is high. Accordingly, a high pressure gradient is present.

The high pressure gradient in the feed system ensures the high energy reserve in the melt. This energy reserve in the melt has the same function as for example a biased spring.

When the melt is introduced into the entrance of the mould cavity the energy reserve in the melt ensures, that the spring effect in the melt when released will substantially fill the mould cavity in a very short time. By "substantially fill" is meant that the mould cavity is filled with melt within predetermined tolerances for needles produced.

Surprisingly, it has been found, that due to the energy reserve in the melt, the high melt pressure in front of the screw can be transferred to the flow front of the melt in approximately 1 msec. Hereby, the solidification or freezing of the melt before the melt actually has substantially filled the entire mould cavity is avoided.

Accordingly, the entire mould cavity will substantially be filled by the melt, so the predetermined length and diameter of the needles is obtained.

A third object of the invention relates to a plastic needle having two ends, said needle being produced by injection moulding from a plastic melt, wherein the outer diameter of the moulded needle in at least one end of the needle is less than 0.50 mm, preferably less than 0.45 mm, said needle comprising a lumen.

Hereby, a plastic needle is obtained having an outer diameter, which diameter is so thin that the pain as well as the tissue damage resulting from injections is reduced. Especially for diabetics who are injecting insulin several times a day the thin needle is useful.

In an embodiment according to the invention the inner diameter of the needle, e.g. the diameter of the lumen, may correspond to at most 60% of the outer diameter of the needle, preferably from 20% to 50% of the outer diameter. Hereby, a high strength of the needle is obtained compared to the size of the inner diameter.

The lumen may be formed in many different ways. In one embodiment according to the invention an insert in the mould cavity corresponding to the lumen of the needle may form the lumen.

In another embodiment the insert may comprise a wire substantially centred in the mould cavity for forming the lumen in the needle. According to the invention the wire may be fixed extending through the entire mould cavity. Hereby, the melt flows around the wire and the lumen is formed.

After the melt has solidified and the needle is formed the wire is removed from the needle. For example, means may be arranged for removing the wire after moulding. The removal of the wire may be carried out before or after the needle leaves the mould cavity.

The pressure is increased gradually through the feed system to meet the specific pressure demands at the entrance of the mould cavity. The pressure increase may be carried out by any suitable means.

In one embodiment the specific design of the feed system, i.e. the geometry of the feed system, leads to an increase of the pressure.

The feed system may be comprised of a long tube having a small diameter, optionally with parts of decreasing diameter.

The diameter of the feed system may be decreased in many suitable ways such as stepwise or continuously. In one embodiment according to the invention the feed system is at least partly of conical shape, or in another embodiment the feed system comprises cylindrical parts of different diameters separated by conical parts, whereby the pressure is increased gradually through the feed system. It is of importance to ensure that a sudden increase of pressure is avoided in the feed system.

The amount of melt being introduced into the feed system shall be of a rate sufficient to fill at least the feed system completely in a predetermined time interval, so the design of the feed system can increase the pressure to a level which is enough for completely filling the mould cavity.

If the rate introduced is too small, the feed system will not be timely filled and accordingly the pressure will not be increased sufficiently to eventually fill the mould cavity.

In cases where the rate introduced is to large, it is not possible to control the increase of the pressure and thereby the complete filling of the mould cavity.

Therefore, the melt is preferably introduced into the feed system with a rate of from 0.10 to 100 ccm/sec, preferably from 1 to 10 ccm/sec.

The feed system and mould cavity may exhibit many different temperatures according to the material used in moulding process. The temperature of the feed system and mould cavity has a direct influence on the viscosity of the melt and thereby the ability of the melt to flow easily through the feed system and the mould cavity. However, the temperature may not be to high as this will influence on the strength of the produced needle.

According to the invention the temperature of the feed system and of the mould cavity may be from 50 to 350° C., preferably from 120 to 140° C. Hereby, the flow length of the melt in the feed system and in the mould cavity is optimal in relation to the strength of the produced needle.

In a preferred embodiment according to the invention a ring gate is arranged in front of the mould cavity, so the melt is introduced into the ring gate before entering the mould cavity. The melt will in this embodiment be completely confluent along the periphery of the ring gate before entering the mould cavity in order to avoid a burr or any other moulding defects due to lack of confluence.

The ring gate may have many different shapes. In one embodiment the ring gate is of a conical shape. When the ring gate have an elongated conical shape, no sudden changes in the thickness of the melt material will occur and the melt flow will not stop.

Especially in cases where a wire is substantially centred in the ring gate and the mould cavity for forming the lumen, the melt may be introduced radially into the ring gate. A suitable balance of the melt in the ring gate is hereby obtained. The melt will flow equally around the wire and will have a uniform flow front and thereby distribution in the mould cavity. Hereby, the produced needle avoid having a burr or any other moulding defects.

In order to avoid that the plastic melt will freeze or solidify in the mould cavity, the melt has to be introduced into the mould cavity in a short time. According to the present invention the mould cavity may be substantially filled in a period of time from 0.1 to 10 msec, preferably from 1 to 2 msec. Hereby, the entire mould cavity will be filled with the melt before it starts to solidify or to freeze.

The plastic needle is preferably produced from a liquid crystalline polymer melt. The material, liquid crystalline polymer, may be used due to the fact, that it has a high degree of molecular orientation. During moulding the molecules of the liquid crystalline polymer melt are aligned substantially in the direction of the main flow of the melt. After solidification of the liquid crystalline polymer the molecular orientation is maintained. This high degree of orientation of the material ensures that the needles obtained exhibits high strength compared to needles made of other plastic materials.

The liquid crystalline polymer may be a polymer comprising monomer units selected from hydroxybenzoic acid, hydroxynaphtoic acid, terephtalic acid, p-aminophenol and p-biphenol alone or in combination.

In an embodiment according to the invention the polymer may be a random copolymer comprising 70–80% hydroxybenzoic acid and 20–30% hydroxynaphtoic acid.

The passage of the melt in the feed system ensures a gradually increase in pressure, the passage furthermore ensures that an optimal orientation of the material particles in the plastic melt is obtained. Hereby, a needle with the necessary strength is obtained.

In order to increase the strength of the needle, the plastic melt may comprise fibre reinforcement. The reinforcement may be selected from glass fibre, carbon fibre, aramid fibre or any suitable fibres.

When the melt comprises fibre reinforcement the viscosity of the melt is increased and thereby it's ability to flow is decreased. For obtaining a sufficient strength of the needle in relation to the viscosity of the melt, the reinforcement fibres may constitute from 15 to 40% by weight of the solid plastic, preferably from 25 to 35%, such as approximately 30%.

DETAILED DESCRIPTION

Figure 2:
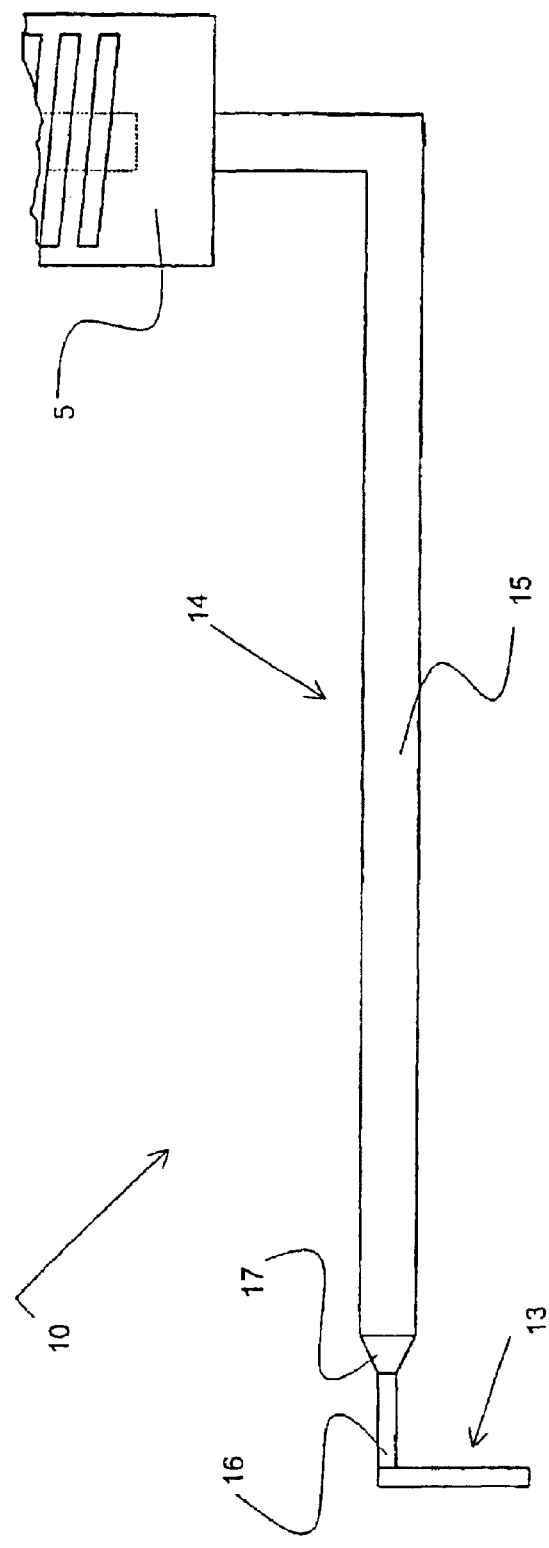
Figure 3:
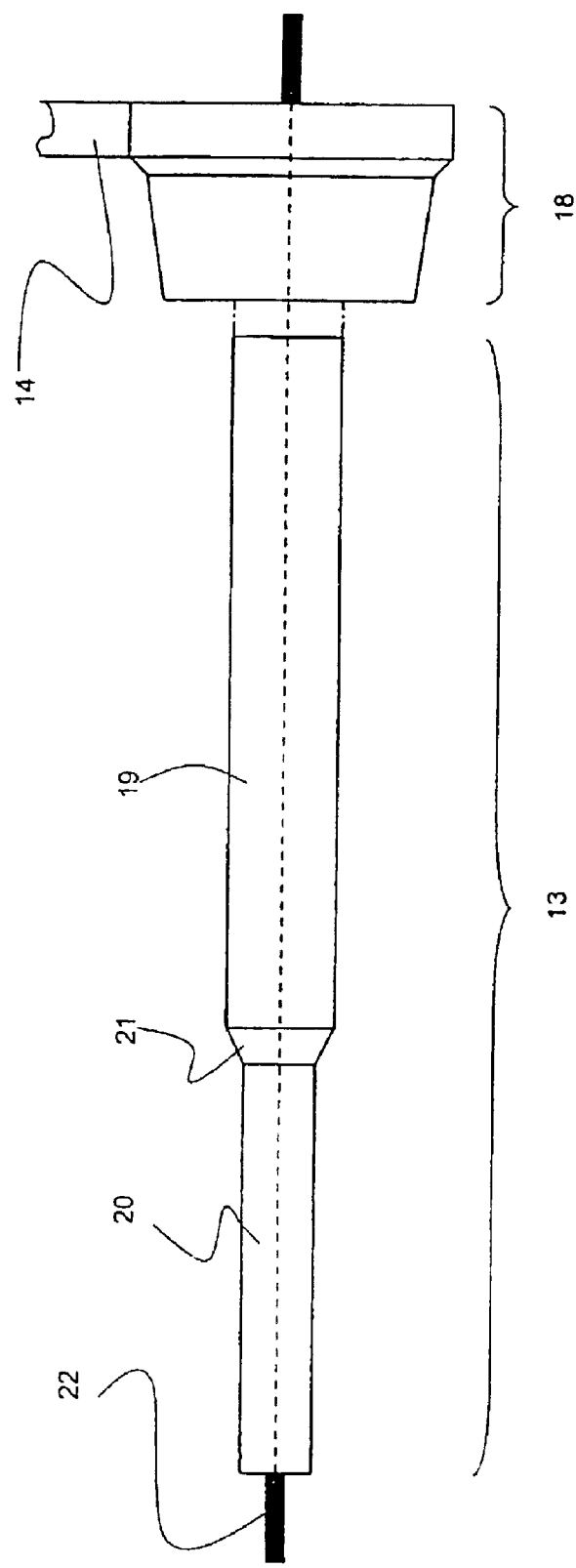
Figure 4:
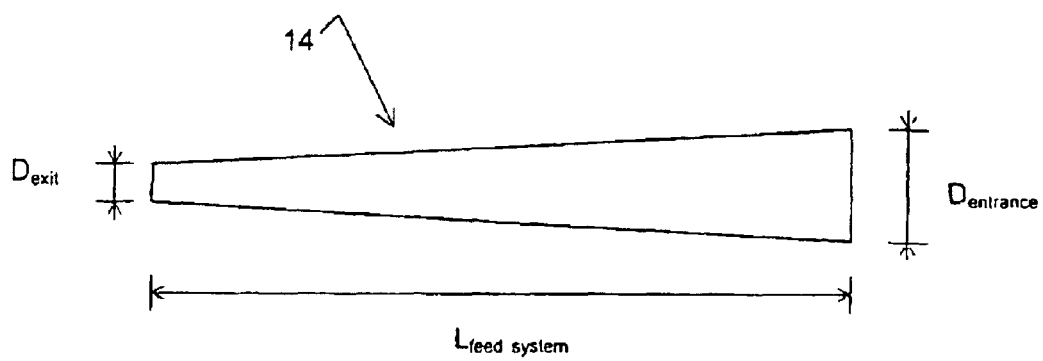
Figure 5:
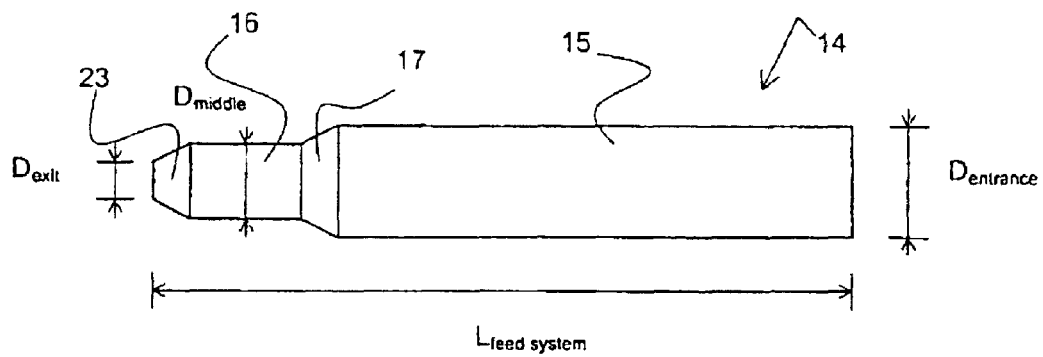
Figure 6:
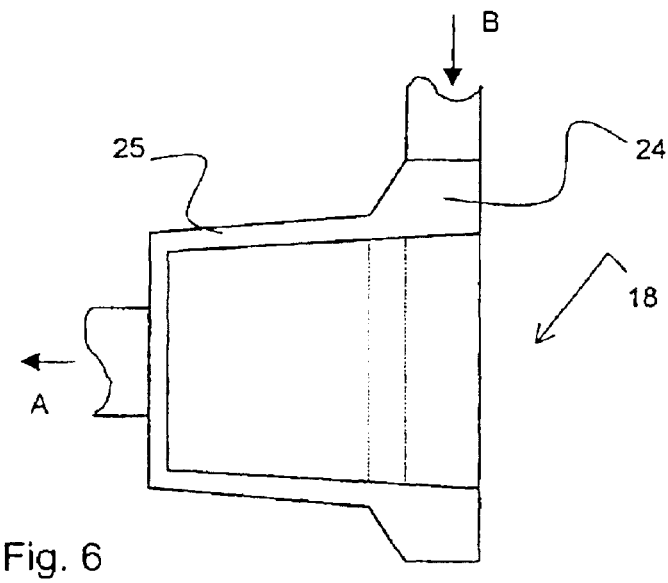
Figure 7:
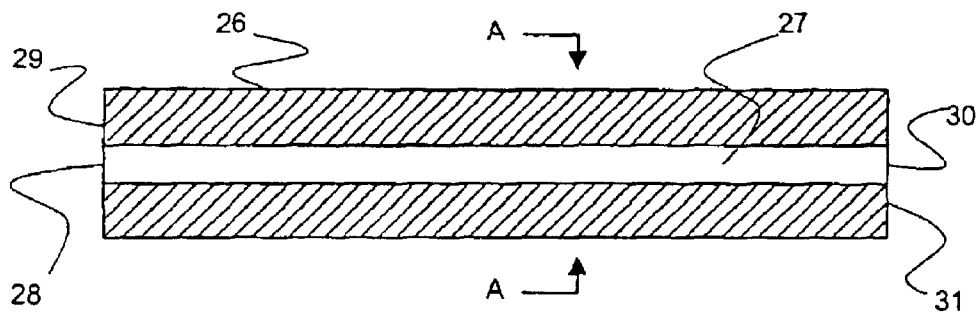

The invention will be explained more fully below with reference to particularly preferred embodiments as well as the drawing, in which FIG. 1 is a schematic view of an injection moulding system according to the invention, FIG. 2 is a schematic view of an assembly comprising the mould cavity and the feed system, FIG. 3 is a schematic view of the mould cavity and a ring gate, FIG. 4 is a schematic view of a first embodiment of the feed system according to the invention, FIG. 5 is a schematic view of a second embodiment of the feed system according to the invention, FIG. 6 is a sectional view of the ring gate shown in FIG. 3, FIG. 7 is a schematic sectional view of the plastic needle.

Figure 8:
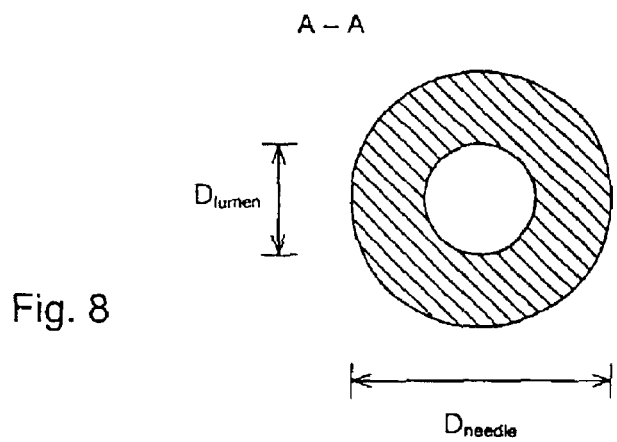
Figure 9:
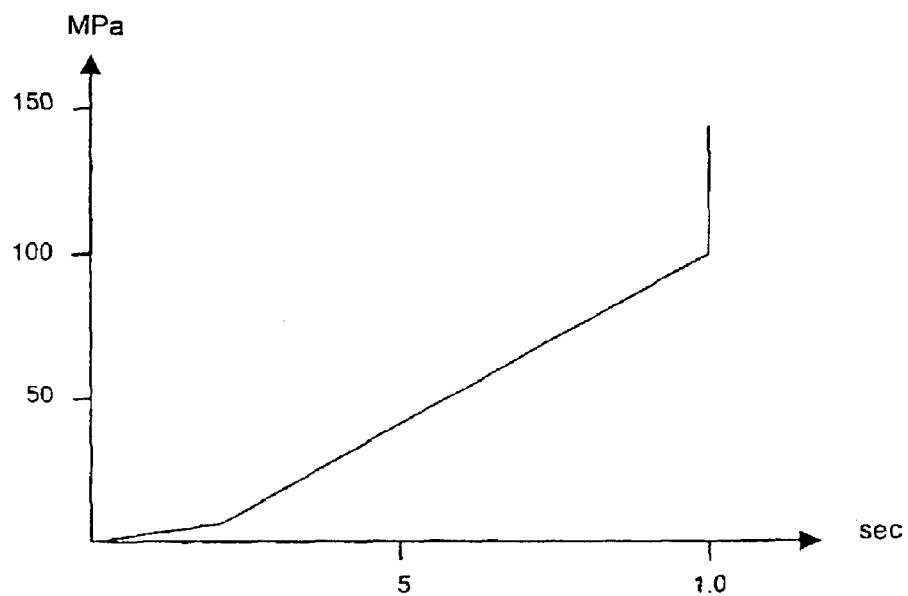

FIG. 8 is a schematic sectional view of the vertical section A—A shown in FIG. 6, and FIG. 9 is a view of a diagram showing the pressure as function of the time.

All the figures are highly schematic and not necessarily to scale, and they show only parts which are necessary in order to elucidate the invention, other parts being omitted or merely suggested.

The moulding system 1 may be any injection moulding system suitable for injection moulding of small articles. In FIG. 1 is shown a schematic view of a injection moulding system 1.

The system 1 comprises a granulate reservoir 2, which reservoir 2 contains the plastic in a solid phase.

The granulate is at the bottom 3 of the reservoir 2 lead through a feed tube 4 into a chamber 5. In this embodiment the chamber 5 comprises a screw 6, which screw 6 is rotated by a driving shaft 7 connected to a motor 8. An instrument for measuring pressure 9 is connected to the chamber 5 in front of the screw 6, for monitoring the pressure building by the screw 6. As the screw 6 rotates the granulate is led towards the entrance of an assembly 10. During the rotation of the screw 6 the granulate is being heated and becomes a plastic melt. The temperature is monitored by a temperature sensor 11.

The temperature of the assembly 10 is monitored by a temperature sensor 12 and is controlled to be from 50 to 350° C., preferably from 120 to 140° C. according to the material used in the moulding process. Hereby, the flow length of the melt in the assembly 10 is optimal in relation to the strength of the produced needle.

The assembly 10 is shown schematic in FIG. 2. The assembly 10 comprises in this embodiment a mould cavity 13 and a feed system 14.

The melt from the chamber 5 is introduced into the feed system 14. From the feed system 14 the melt is introduced radially into the mould cavity 13. In the feed system 14 the melt pressure is gradually increased before the melt enters the mould cavity 13.

In the embodiment shown in FIG. 2 the pressure is increased due to the distance the melt has to flow. The matter is that the pressure is increased due to the flow resistance of the melt. The pressure is furthermore increased by decreasing the diameter of the feed system 14. The feed system 14 comprises a first cylindrical part 15 having a first diameter and a second cylindrical part 16 having a second diameter, smaller than the first diameter. The first cylindrical part 15 is separated from the second cylindrical part 16 by a conical part 17.

The melt pressure in this embodiment is already increased from the start of the feed system 14 and afterwards increased gradually by the passage of the melt through the feed system 14 due to the distance the melt has to flow as well as due to the decreasing of the diameter of the feed system 14.

The melt pressure is increased sufficiently so the high energy reserve in the melt is ensured. Hereby, the melt pressure can be transferred to the flow front of the melt in approximately 1 msec.

In FIG. 3 is the mould cavity 13 shown separated from a ring gate 18, the function of the ring gate 18 will be explained more fully below. The melt is in this embodiment introduced radially from the feed system 14 into the ring gate 18 in respect to the melt flow in the mould cavity 13. The mould cavity 13 comprises a first part 19 having a first diameter and a second part 20 with a second diameter smaller than the first diameter. The first part 19 is separated from the second part 20 by a conical part 21. The diameter of the second part 20 corresponds to the outer diameter of the needle and is less than 0.50 mm.

A wire 22 is substantially centred in the mould cavity 13 for forming the lumen in the needle. In this embodiment the wire 22 is fixed and extends through the mould cavity 13 and further through the ring gate 18. Hereby the melt flows equally around the wire during moulding and the lumen is formed in the centre of the needle.

In FIG. 4 another embodiment of the feed system 14 according to the invention is shown. The feed system 14 has in this embodiment a first diameter $D_{entrance}$ at the entrance to the feed system 14 and a second diameter $D_{exit}$ at the exit of the feed system 14. The diameter of the feed system 14 is in this embodiment gradually decreasing along the entire length $L_{feed\ system}$, so the feed system 14 exhibits a conical geometry.

In FIG. 5 is the feed system 14 shown in the same way as in FIG. 2. In this embodiment the feed system 14 is having two cylindrical parts separated by conical parts. The first cylindrical part 15 is having a diameter corresponding to the diameter $D_{entrance}$ at the entrance to the feed system 14. The second cylindrical part 16 is having a diameter $D_{middle}$, which diameter $D_{middle}$ is smaller than the diameter $D_{entrance}$. At the end of the feed system 14 the diameter corresponds to the diameter $D_{exit}$, which diameter corresponds to the entrance of the mould cavity. The first cylindrical part 15 is separated from the second cylindrical part 16 by a first conical part 17. The second cylindrical part 16 is further separated from the mould cavity by a second conical part 23. The diameter of the feed system 14 is in this embodiment decreased in steps along its entire length $L_{feed\ system}$.

In FIG. 6 is a schematic sectional view of the ring gate 18 shown. The arrow B indicates the main melt flow direction in the feed system. The melt is introduced radially into the ring gate 18 (indicated by arrow B) with respect to the melt flow in the mould cavity (indicated by arrow A). A first part 24 of the ring gate 18, where the melt is introduced, is formed with a large volume around the circumference of the ring gate 18, whereby the melt is forced to flow firstly along the circumference of the first part 24 filling the large volume with melt before entering a second part 25 of the ring gate 18. In the second part 25 the melt flows in direction of arrow A. The second part 25 of the ring gate 18 is designed with an elongated conical geometry to avoid any sudden changes in geometry that otherwise could lead to melt stop.

In FIG. 7 a schematic sectional view of a plastic needle 26 is shown. The needle 26 is having a longitudinal lumen 27 extending between one opening 28 at a first end 29 of the needle 26 and a second opening 30 at a second end 31.

FIG. 8 shows a sectional view of the vertical section A—A of the needle 26. In this embodiment the needle 26 is round and has an outer diameter $D_{needle}$ as well as an inner diameter $D_{lumen}$.

A plastic needle being produced according to the invention having an outer diameter of 0.40 mm and a length of 8.00 mm. The needle is further having a lumen with a diameter of 0.16 mm. The wall of the needle is in this embodiment 0.12 mm.

The plastic melt used is a liquid crystalline polymer, which is a random copolymer comprising 73% hydroxybenzoic acid and 27% hydroxynaphtoic acid.

The needle is being produced in an injecting moulding system having an assembly comprising a feed system, a ring gate as well as a mould cavity.

The screw used in the injecting moulding system has a 15 mm screw. The injection moulding system is set to introduce approximately 2.6 ccm of melt into the feed system with an injection speed of 3 ccm/sec. The temperature of the assembly is controlled to 130–140° C.

The geometrical form of the feed system is as follows, an entrance diameter of 4.00 mm, a first cylindrical part with a diameter of 2.50 mm for distance of 449.00 mm, a second cylindrical part with a diameter on 1.60 mm for a distance of 10.00 mm, separated by a conical part for a distance of 10.00 mm.

The diagram in FIG. 9 shows an abscissa and an ordinate. At the abscissa the time is indicated as seconds, and at the ordinate the pressure is indicated as MPa. The diagram shows the melt pressure at the entrance to the feed system as function of the time during filling of the assembly. In the diagram it is shown, that the pressure is being increased gradually for about a second during the melts passage of the feed system. At about 1 sec on the abscissa, the pressure have a high increase due to the small diameter of the mould cavity. The high pressure in the melt will due to the energy reserve be transferred to the flow front of the melt, so the entire mould cavity will be filled before the melt starts to solidify.

Hereby, the pressure of the melt will be increased during passage of the feed system, so the energy reserve in the melt will be sufficient to fill the entire mould cavity in approximately 1 msec. Accordingly, the produced needle will obtain the predetermined size as mentioned before.

What is claimed is:

1. A method for producing a plastic needle, which needle has two ends, wherein at least the outer diameter of one end is less than 0.50 mm, said needle further having a longitudinal lumen extending between two openings of the needle, in a moulding system having an assembly comprising a feed system and a mould cavity, wherein an insert is corresponding to the lumen of the needle for forming the lumen in the needle, said method comprising the following steps:

introducing a melt of plastic into the feed system, increasing the melt pressure gradually during melt passage through the feed system, passing the melt into the mould cavity whereby the melt solidifies to a needle, the mould cavity being substantially filled in a period of time from 0.1 to 10 msec, and removing the needle from the mould cavity.

2. The method according to claim 1, wherein the melt is introduced into the feed system with a rate of from 0.10 to 100 ccm/sec.

3. The method according to claim 1, wherein the mould temperature is from 50 to 350° C.

4. The method of claim 2, wherein the rate is from 1 to 10 ccm/sec.

5. The method of claim 3, wherein the mould temperature is from 120 to 140° C.

6. A method for producing a plastic needle, which needle has two ends, wherein at least the outer diameter of one end is less than 0.50 mm, said needle further having a longitudinal lumen extending between two openings of the needle, in a moulding system having an assembly comprising a feed system and a mould cavity, wherein an insert is corresponding to the lumen of the needle for forming the lumen in the needle, said method comprising the following steps:

introducing a melt of plastic into the feed system, increasing the melt pressure gradually during melt passage through the feed system, passing the melt into the mould cavity whereby the melt solidifies to a needle, the mould cavity being substantially filled in a period of time from 1 to 2 msec, and removing the needle from the mould cavity.

* * * * *